(12) United States Patent
Darrah et al.

(10) Patent No.: US 12,372,524 B2
(45) Date of Patent: Jul. 29, 2025

(54) ANTI-PAD2 ANTIBODY FOR TREATING AND EVALUATING AUTOIMMUNE AND INFLAMMATORY DISEASES

(71) Applicant: The Johns Hopkins University, Baltimore, MD (US)

(72) Inventors: Erika L. Darrah, Baltimore, MD (US); Felipe Andrade, Timonium, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 0 days.

(21) Appl. No.: 18/111,179

(22) Filed: Feb. 17, 2023

(65) Prior Publication Data
US 2023/0204577 A1 Jun. 29, 2023

Related U.S. Application Data

(62) Division of application No. 15/945,411, filed on Apr. 4, 2018, now abandoned.

(60) Provisional application No. 62/481,158, filed on Apr. 4, 2017.

(51) Int. Cl.
| | |
|---|---|
| G01N 33/564 | (2006.01) |
| A61K 39/00 | (2006.01) |
| A61K 39/395 | (2006.01) |
| A61P 19/02 | (2006.01) |
| A61P 29/00 | (2006.01) |
| A61P 37/06 | (2006.01) |
| C07K 16/40 | (2006.01) |

(52) U.S. Cl.
CPC ....... *G01N 33/564* (2013.01); *A61K 39/0008* (2013.01); *A61K 39/39533* (2013.01); *A61P 19/02* (2018.01); *A61P 29/00* (2018.01); *A61P 37/06* (2018.01); *C07K 16/40* (2013.01); *C12Y 305/03015* (2013.01); *C07K 2317/24* (2013.01); *C07K 2317/76* (2013.01); *G01N 2333/978* (2013.01); *G01N 2800/24* (2013.01); *G01N 2800/50* (2013.01); *G01N 2800/52* (2013.01); *G01N 2800/7095* (2013.01)

(58) Field of Classification Search
None
See application file for complete search history.

(56) References Cited

U.S. PATENT DOCUMENTS

| | | |
|---|---|---|
| 5,514,548 A | 5/1996 | Krebber et al. |
| 5,545,806 A | 8/1996 | Lonberg et al. |
| 5,569,825 A | 10/1996 | Lonberg et al. |
| 6,265,150 B1 | 7/2001 | Terstappen et al. |
| 9,417,247 B2 | 8/2016 | Rosen et al. |
| 2002/0197266 A1 | 12/2002 | Debinski |
| 2015/0031048 A1* | 1/2015 | Van Eyk ............ G01N 33/6848 435/7.92 |
| 2015/0376294 A1 | 12/2015 | Nielsen et al. |
| 2016/0061824 A1 | 3/2016 | Hahn et al. |
| 2016/0355565 A1 | 12/2016 | Stoecker |

FOREIGN PATENT DOCUMENTS

| | | |
|---|---|---|
| WO | 93/06213 | 4/1993 |
| WO | 1994/13804 | 6/1994 |
| WO | 2014037911 | 3/2014 |
| WO | 2015169602 | 11/2015 |
| WO | 2016155745 | 10/2016 |
| WO | 2016183310 A1 | 11/2016 |

OTHER PUBLICATIONS

Damgaard et al. Generation of monoclonal antibodies against peptidylarginine deiminase 2 (PAD2) and development of a PAD2-specific enzyme-linked immunosorbent assay(Journal of Immunological Methods, 405 (2014) 15-22) (Year: 2014).*
Darrah et al. Autoantibodies to Peptidylarginine Deiminase 2 Protect Against Radiographic Progression in Patients with Rheumatoid Arthritis. (Abstract 3022: 2016 ACR/ARHP Meeting; first published Sep. 28, 2016) (Year: 2016).*
Arend WP, et al. Pre-rheumatoid arthritis: predisposition and transition to clinical synovitis. Nat Rev Rheumatol Oct. 2012; 8(10):573-86.
Vossenaar et al., PAD, a growing family of citrullinating enzymes: genes, features and involvement in disease. Bioessays Nov. 2003;25(11):1106-18.
Chang X, et al. PADI2 is significantly associated with rheumatoid arthritis. PLoS One; Dec. 5, 2013;8(12):e81259.\.
Suzuki, A, et al. Functional haplotypes of PADI4, encoding citrullinating enzyme peptidylarginine deiminase 4, are associated with rheumatoid arthritis. Nat Genet; Aug. 2003;34(4):395-402.
Darrah, E, et al. Peptidylarginine deiminase 2, 3 and 4 have distinct specificities against cellular substrates: novel insights into autoantigen selection in rheumatoid arthritis. Ann Rheum Dis Jan. 2012;71(1):92-8.
Willis, VC, et al. N-alpha-benzoyl-N5-(2-chloro-1-iminoethyl)-L-ornithine amide, a protein arginine deiminase inhibitor, reduces the severity of murine collagen-induced arthritis. J Immunol; Apr. 1, 2011;186(7):4396-404.
Kawalkowska J, et al. Abrogation of collagen-induced arthritis by a peptidyl arginine deiminase inhibitor is associated with modulation of T cell-mediated immune responses. Sci Rep; May 23, 2016;6:26430.
Harris, ML, et al. Association of autoimmunity to peptidyl arginine deiminase type 4 with genotype and disease severity in rheumatoid arthritis. Arthritis Rheum; Jul. 2008;58(7):1958-67.

(Continued)

*Primary Examiner* — Janet L Andres
*Assistant Examiner* — Brian Hartnett
(74) *Attorney, Agent, or Firm* — Tarolli, Sundheim, Covell & Tummino LLP

(57) ABSTRACT

A method for measuring anti-PAD2 antibodies in a subject with an inflammatory or autoimmune disease, and to determine if the subject has a better prognosis for developing a more severe form of inflammation based on anti-PAD2 antibody levels. Methods for the therapeutic use of anti-PAD2 antibodies are also described.

7 Claims, 4 Drawing Sheets

(56) References Cited

OTHER PUBLICATIONS

Halvorsen, EH, et al. Serum IgG antibodies to peptidylarginine deiminase 4 predict radiographic progression in patients with rheumatoid arthritis treated with tumour necrosis factor-alpha blocking agents. Ann Rheum Dis; Feb. 2009;68(2):249-52.
Darrah, E, et al. Erosive rheumatoid arthritis is associated with antibodies that activate PAD4 by increasing calcium sensitivity. Sci Transl Med; May 22, 2013;5(186):186ra65.
Giles, JT, et al. Association of cross-reactive antibodies targeting peptidyl-arginine deiminase 3 and 4 with rheumatoid arthritis-associated interstitial lung disease. PLoS One; Jun. 5, 2014;9(6):e98794.
Giles, JT, et al. Association of fine specificity and repertoire expansion of anticitrullinated peptide antibodies with rheumatoid arthritis associated interstitial lung disease. Ann Rheum Dis; Aug. 2014;73(8):1487-94.
Romero, V, et al. Immune-mediated pore-forming pathways induce cellular hypercitrullination and generate citrullinated autoantigens in rheumatoid arthritis. Sci Transl Med; Oct. 30, 2013;5(209):209ra150.
Damgaard, D, et al. Demonstration of extracellular peptidylarginine deiminase (PAD) activity in synovial fluid of patients with rheumatoid arthritis using a novel assay for citrullination of fibrinogen. Arthritis Res Ther; Dec. 5, 2014;16 (6):498.
Masson-Bessiere, C, et al. The major synovial targets of the rheumatoid arthritis-specific antifilaggrin autoantibodies are deiminated forms of the alpha- and beta-chains of fibrin. J Immunol; Mar. 15, 2001;166(6):4177-84.
Zhang, X, et al. Peptidylarginine deiminase 2-catalyzed histone H3 arginine 26 citrullination facilitates estrogen receptor alpha target gene activation. Proc Natl Acad Sci U S A; Aug. 14, 2012;109(33):13331-6.
Ward, et al., 1989, Nature 341:544-546.
Bird, et al., 1988, Science 242:423-426.
Huston, et al., 1988, Proc. Natl. Acad. Sci. U.S.A. 85:5879-5883.
Tomlinson, et al., 2000, Methods Enzymol. 326:461-479.
Hollinger, et al., 1993, Proc. Natl. Acad. Sci. U.S.A. 90:6444-6448.
Coloma & Morisson 1997, Nature Biotechnology 15, 159-163.
Blade et al., ACS Chem Biol. 10(4), 1043-53 (2015).
Kohler and Milstein Eur. J. Immunol., 5, 511-519 (1976).
Haskard and Archer J. Immunol. Methods, 74(2), 361-67 (1984).
Roder, et al., Methods Enzymol., 121, 140-67 (1986).
Huse et al., Science, 246, 1275-81 (1989).
Kamman, M., et al., Nucl. Acids Res., 17: 5404 (1989).
Sato K., et al., Cancer Research, 53: 851-856 (1993).
Daugherty, B. L. et al., Nucleic Acids Res., 19(9): 2471-2476 (1991).
Lewis, A. P., et al., Gene, 101: 297-302 (1991).
Damgaard Dres, et al. "Generation of monoclonal antibodies against peptidylarginine deiminase 2 (PAD2) and development of a PAD2-specific enzyme-linked immunosorbent assay." Journal of Immunological Methods 405 (2014): 15-22.

\* cited by examiner

ANTI-PAD2 ANTIBODY FOR TREATING AND EVALUATING AUTOIMMUNE AND INFLAMMATORY DISEASES

CONTINUING APPLICATION DATA

The present application is a Divisional Application of U.S. patent application Ser. No. 15/945,411, filed Apr. 4, 2018, which claims the benefit of U.S. Provisional Application Ser. No. 62/481,158, filed Apr. 4, 2017, the entirety of these applications is hereby incorporated by reference for all purposes.

GOVERNMENT FUNDING

This invention was made with government support under grant number NIH NIAMS AR050026-10 awarded by the National Institutes of Health. The government has certain rights in this invention.

BACKGROUND

Accumulating evidence suggests that enzymatic deamination of arginines in proteins (or citrullination), a process catalyzed by the peptidylarginine deiminase (PAD) enzymes, plays a pathogenic role in several autoimmune and inflammatory diseases including Alzheimer's disease, multiple sclerosis (MS), psoriasis, rheumatoid arthritis (RA), ulcerative colitis, and cancer. Witalison et al., Curr Drug Targets, 16(7):700-710 (2015).

There are five members of the PAD enzyme family (PAD1, PAD2, PAD3, PAD4, and PAD6), which display diverse tissue distribution and substrate specificity. Interestingly, autoantibodies to PAD4 are present in ~35% of patients with RA and are associated with erosive disease that persists despite treatment with TNFα inhibitors. Harris et al., Arthritis Rheum, 58(7):1958-1967 (2008). Moreover, a subgroup of anti-PAD4 antibodies that cross react with PAD3 (anti-PAD3/4 antibodies) has recently been identified. These antibodies have the capacity to activate the PAD4 enzyme by lowering the amount of calcium required for catalysis. Patients with anti-PAD3/4 antibodies have the most erosive RA that progresses despite treatment with standard therapies and are at the highest risk of having RA-associated interstitial lung disease (RA-ILD). Darrah et al., Sci Transl Med, 5(186):186ra65 (2013). Despite a similarly important role for PAD2 in RA pathogenesis, it is unknown whether this enzyme is also a target of the humoral response in RA. Moreover, it is unknown if PAD2 is also a target of antibodies in other inflammatory and autoimmune diseases. In this study, we developed an assay to detect anti-PAD2 antibodies in subjects having conditions in which PAD2 is suspected to play a pathogenic role.

SUMMARY OF THE INVENTION

Peptidylarginine deiminases (PADs) are key enzymes implicated in the pathogenesis of autoimmune and inflammatory diseases. Here, we developed an assay to detect antibodies to the PAD2 enzyme in biological samples. The presence of anti-PAD2 antibodies using this novel assay was initially established using samples from patients with RA, MS and psoriatic arthritis (PsA). The clinical significance of anti-PAD2 antibodies was further validated in patients with RA.

A PAD2 ELISA assay was established to screen for anti-PAD2 antibodies in sera. Samples from RA, MS, and PsA patients, as well as healthy controls were used to validate the assay. In addition, the clinical and demographic characteristics of RA patients were compared according to their anti-PAD2 antibody status and level. Multivariable models were constructed to explore the independent associations of anti-PAD2 antibodies with clinical variables in RA. The frequency of anti-PAD2 antibodies in RA, MS and PsA patients was 18.5-22%, depending on the condition. Among RA patients, anti-PAD2 antibodies were inversely associated with HLA-DRβ1 shared epitope alleles, swollen joint count, and interstitial lung disease (ILD), and were not associated with seropositive disease. After adjusting for relevant confounders, anti-PAD2 antibodies were independently and significantly associated with fewer swollen joints, a lower frequency of ILD, and less progression of radiographic joint damage in RA. Interestingly, anti-PAD2 antibodies in RA did not affect PAD2 enzymatic activity, suggesting alternative mechanism(s) for how these antibodies may contribute to a milder disease phenotype. The anti-PAD2 ELISA assay is useful to detect antibodies to PAD2 in several inflammatory and autoimmune diseases. These antibodies are present in distinct subgroups of patients with RA, MS and PsA. Moreover, anti-PAD2 antibodies represent a novel serologic marker in RA that identifies a genetically and clinically unique subset of patients with less severe joint and lung disease.

BRIEF DESCRIPTION OF THE FIGURES

The present invention may be more readily understood by reference to the following figures, wherein.

DETAILED DESCRIPTION OF THE INVENTION

Figure 1:
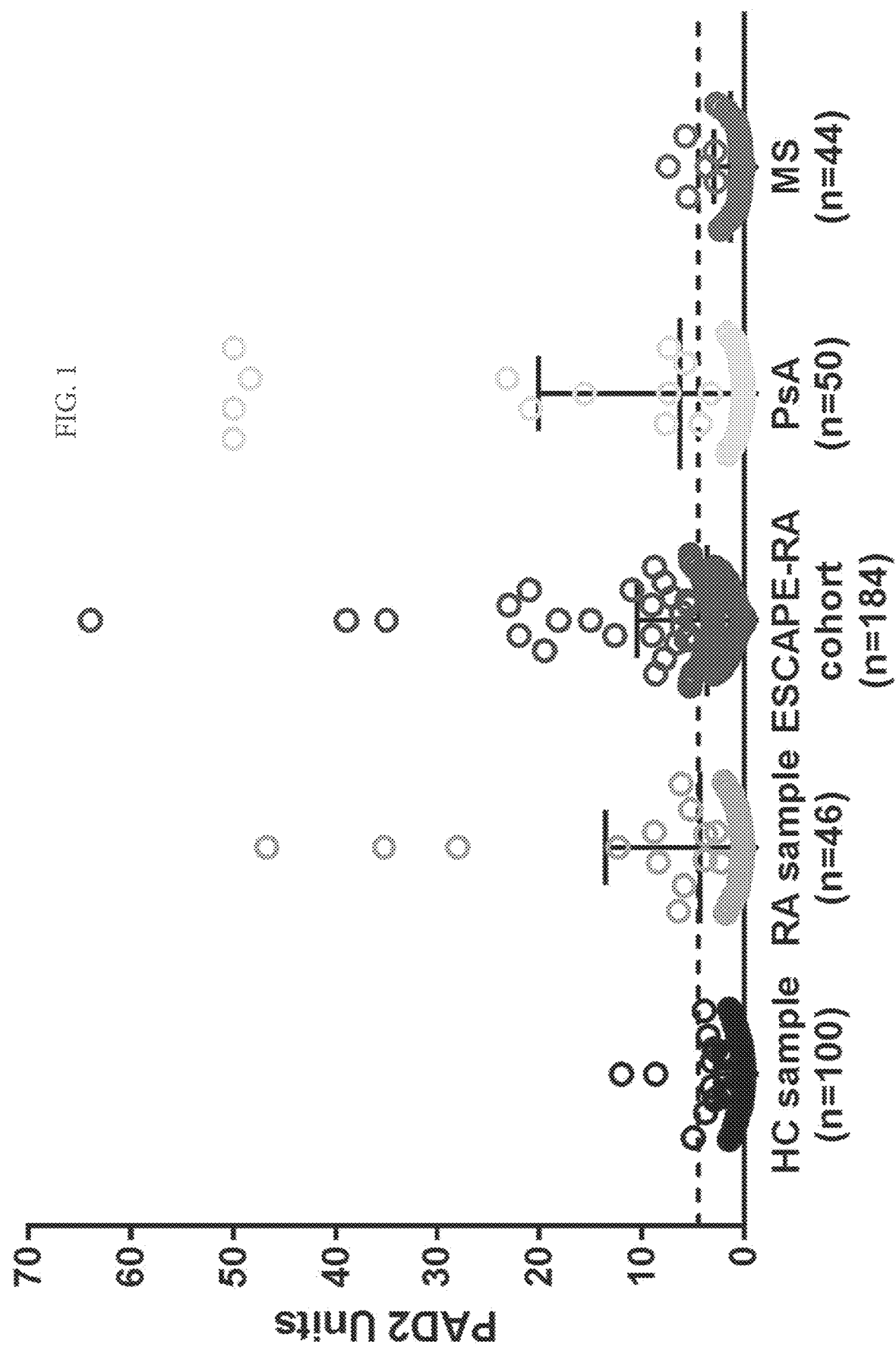
FIG. 1 provides a graph showing the utility of the anti-PAD2 ELISA to detect anti-PAD2 antibodies in different inflammatory and autoimmune conditions, including RA, MS and PsA. Anti-PAD2 antibody arbitrary units (AU) are plotted for each patient and healthy control (HC) serum tested. The cutoff for anti-PAD2 positivity is indicated (---) and was set at 3-standard-deviations above the mean of the HC sample. The mean and standard deviation for each group of sera are shown. The mean anti-PAD2 levels in the disease groups was compared to the healthy controls and a p<0.05 was considered significant.

Unless otherwise defined, all technical and scientific terms used herein have the same meaning as commonly understood by one of ordinary skill in the art to which these exemplary embodiments belong. The terminology used in the description herein is for describing particular exemplary embodiments only and is not intended to be limiting of the exemplary embodiments. As used in the specification and the appended claims, the singular forms "a," "an," and "the" are intended to include the plural forms as well, unless the context clearly indicates otherwise. All publications, patent applications, patents, and other references mentioned herein are incorporated by reference in their entirety.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

"Treating", as used herein, means ameliorating the effects of, or delaying, halting or reversing the progress of a disease or disorder. The word encompasses reducing the severity of a symptom of a disease or disorder and/or the frequency of a symptom of a disease or disorder. A subject is successfully "treated" for a disorder characterized by increased autoantibody (AA) levels if the subject shows observable and/or measurable reduction in or absence of one or more signs and symptoms of a particular disease or condition.

A "subject", as used therein, can be a human or non-human animal. Non-human animals include, for example, livestock and pets, such as ovine, bovine, porcine, canine, feline and murine mammals, as well as reptiles, birds and fish. Preferably, the subject is human.

The language "effective amount" or "therapeutically effective amount" refers to a nontoxic but sufficient amount of the composition used in the practice of the invention that is effective to provide effective treatment in a subject. That result can be reduction and/or alleviation of the signs, symptoms, or causes of a disease or disorder, or any other desired alteration of a biological system. An appropriate therapeutic amount in any individual case may be determined by one of ordinary skill in the art using routine experimentation.

The term antibody, as used herein and unless further limited, refers to single chain, two-chain, and multi-chain proteins and glycoproteins belonging to the classes of polyclonal, monoclonal, chimeric and hetero immunoglobulins; it also includes synthetic and genetically engineered variants of these immunoglobulins. The term "Antibody fragment" includes Fab, Fab', F(ab')2, and Fv fragments, as well as any portion of an antibody having specificity toward a desired target epitope or epitopes.

An "autoantibody" (abbreviated "AA") is an antibody produced by the immune system of a subject that is directed against one or more of the subject's own proteins (e.g., PAD2).

Antibodies are grouped into classes, also referred to as isotypes, as determined genetically by the constant region. Human constant light chains are classified as kappa (Cκ) and lambda (Cλ) light chains. Heavy chains are classified as mu, delta, gamma, alpha, or epsilon, and define the antibody's isotype as IgM, IgD, IgG, IgA, and IgE, respectively. The IgG class is the most commonly used for therapeutic purposes. In humans this class comprises subclasses IgG1, IgG2, IgG3, and IgG4. In mice this class comprises subclasses IgG1, IgG2a, IgG2b, IgG3. IgM has subclasses, including, but not limited to, IgM1 and IgM2. IgA has several subclasses, including but not limited to IgA1 and IgA2. Thus, "isotype" as used herein is meant any of the classes or subclasses of immunoglobulins defined by the chemical and antigenic characteristics of their constant regions. The known human immunoglobulin isotypes are IgG1, IgG2, IgG3, IgG4, IgA1, IgA2, IgM1, IgM2, IgD, and IgE.

The term "Fab" or "Fab region" as used herein includes the polypeptides that comprise the VH, CH1, VL, and CL immunoglobulin domains. Fab may refer to this region in isolation, or this region in the context of a full length antibody or antibody fragment.

The term "Fc" or "Fc region", as used herein includes the polypeptide comprising the constant region of an antibody excluding the first constant region immunoglobulin domain. Thus Fc refers to the last two constant region immunoglobulin domains of IgA, IgD, and IgG, and the last three constant region immunoglobulin domains of IgE and IgM, and the flexible hinge N-terminal to these domains.

Antibody fragments include, but are not limited to, (i) the Fab fragment consisting of VL, VH, CL and CH1 domains, including Fab' and Fab'-SH, (ii) the Fd fragment consisting of the VH and CH1 domains, (iii) the Fv fragment consisting of the VL and VH domains of a single antibody; (iv) the dAb fragment (Ward et al., 1989, Nature 341:544-546) which consists of a single variable, (v) F(ab')2 fragments, a bivalent fragment comprising two linked Fab fragments (vi) single chain Fv molecules (scFv), wherein a VH domain and a VL domain are linked by a peptide linker which allows the two domains to associate to form an antigen binding site (Bird et al., 1988, Science 242:423-426, Huston et al., 1988, Proc. Natl. Acad. Sci. U.S.A. 85:5879-5883), (vii) bispecific single chain Fv dimers (PCT/US92/09965), (viii) "diabodies" or "triabodies", multivalent or multi-specific fragments constructed by gene fusion (Tomlinson et. al., 2000, Methods Enzymol. 326:461-479; WO94/13804; Holliger et al., 1993, Proc. Natl. Acad. Sci. U.S.A. 90:6444-6448) and (ix) scFv genetically fused to the same or a different antibody (Coloma & Morrison, 1997, Nature Biotechnology 15, 159-163).

The term antigen, as used herein, refers to a molecule or a portion of a molecule capable of being bound by an antibody which is additionally capable of inducing an animal to produce an antibody capable of binding to an epitope of that antigen. An antigen can have one or more than one epitope. The specific reaction referred to above is meant to indicate that the antigen will react, in a highly selective manner, with its corresponding antibody and not with the multitude of other antibodies which can be evoked by other antigens.

The term epitope, as used herein, refers to that portion of any molecule capable of being recognized by, and bound by, an antibody. In general, epitopes consist of chemically active surface groupings of molecules, for example, amino acids or sugar side chains, and have specific three-dimensional structural characteristics as well as specific charge characteristics. The epitopes of interest for the present invention are epitopes comprising amino acids.

As used herein, the term "capture probe" refers to a molecule capable of binding to a target analyte, e.g., a disease-associated antibody. One example of a capture probe includes antigens that recognize antibodies present in a biological sample including, e.g., but are not limited to, whole blood, plasma, serum, semen, cell lysates, saliva, tears, urine, fecal material, sweat, buccal tissue, skin, synovial fluid, cerebrospinal fluid, and hair, from patients having or suspected of having a disease, e.g., rheumatoid arthritis, Alzheimer's disease, multiple sclerosis, psoriasis, RA, ulcerative colitis, or cancer.

As used herein, the term "immunoassay" refers to an assay in which an antibody (e.g. anti-PAD2) specifically binds, for example, a capture probe recognized by or, including an antigen recognized by, the antibody (e.g. PAD2) to provide for the detection and/or quantitation of the antibody. An "immunoassay" can use a particular capture probe to detect, isolate, target, and/or quantify the antibody that specifically binds to the capture probe. One example of an "immunoassay" includes a capture probe that contains one or more antigens to detect, isolate, and/or quantify one or more antibodies in a sample.

As used herein, the term "particle based multi-analyte test" (PMAT) refers to an assay that allows simultaneous measurement of two or more analytes in a single assay. In some embodiments, a PMAT is a type of multiplex assay. For example, a PMAT can use different types of particles simultaneously, with each type having immobilized a specific capture probe for a specific autoantibody on the surface of its particles. A PMAT can also include a particle with a plurality of capture probes to one or more autoantibodies on the surface of the same particle. The particle can include beads, and other small substrate fragments.

The term monoclonal antibody, as used herein, refers to an antibody obtained from a population of substantially homogeneous antibodies, i.e., the individual antibodies comprising the population are identical and/or bind the same epitope, except for possible variants that may arise during production of the monoclonal antibody, such variants generally being present in minor amounts. In contrast to polyclonal antibody preparations that typically include different antibodies directed against different epitopes, each monoclonal antibody is directed against a single epitope on the antigen. In addition to their specificity, the monoclonal antibodies are advantageous in that they are uncontaminated by other immunoglobulins. The modifier "monoclonal" indicates the character of the antibody as being obtained from a substantially homogeneous population of antibodies.

The term chimeric antibody, as used herein, refers to an antibody which includes sequences derived from two different antibodies, which typically are of different species. Most typically, chimeric antibodies include human and non-human antibody fragments, generally human constant and non-human variable regions.

The term humanized antibody, as used herein, refers to a type of chimeric antibody derived from a non-human antibody, and a human antibody which retains or substantially retains the antigen-binding properties of the parent antibody but which is less immunogenic in humans.

As used herein, a humanized antibody comprises heavy or light chain variable framework regions that are "the product of" or "derived from" a particular human germline sequence (human gene) if the variable framework regions of the antibody are obtained from a system that uses human germline immunoglobulin genes. Such systems include immunizing a transgenic mouse carrying human immunoglobulin genes with the antigen of interest or screening a human immunoglobulin gene library displayed on phage with the antigen of interest. A humanized antibody which comprises a heavy or light chain variable framework region that is "the product of" or "derived from" a human germline immunoglobulin sequence can be identified as such by comparing the amino acid sequence of the heavy or light chain variable framework region of the humanized antibody to the amino acid sequences of the heavy or light chain variable framework region of human germline immunoglobulins. A humanized antibody that comprises a heavy or light chain variable framework region that is "the product of" a particular human germline immunoglobulin sequence has a heavy or light chain variable framework region which is 100% identical in amino acid sequence to the heavy or light chain variable framework region of the particular human germline immunoglobulin sequence. A humanized antibody that comprises a heavy or light chain variable framework region that is "derived from" a particular human germline immunoglobulin sequence may contain amino acid differences as compared to the heavy or light chain variable framework region of the particular germline sequence, due to, for example, naturally-occurring somatic mutations or intentional introduction of site-directed mutation. However, a selected humanized antibody typically is at least 90% identical in amino acid sequence of the heavy or light chain variable framework region to an amino acid sequence encoded by the heavy or light chain variable framework region of a human germline immunoglobulin gene and contains amino acid residues that identify the humanized antibody as being derived from human when compared to the germline immunoglobulin amino acid sequences of other species (e.g., murine germline sequences).

As used herein, the phrase "specifically binds" refers to antibody binding to a target structure, wherein the antibody binds a target structure, or subunit thereof, but does not bind to a biological molecule that is not a target structure. Antibodies that specifically bind to a target structure, or subunit thereof, do not cross-react with biological molecules that are outside the target structure family. An antibody specific for PAD2 can be an antibody or antibody fragment capable of binding to that specific protein with a specific affinity of between $10^{-8}$ M and $10^{-11}$ M. In some embodiments, an antibody or antibody fragment binds to a selected antigen with a specific affinity of greater than $10^{-7}$ M, $10^{-8}$ M, $10^{-9}$ M, $10^{-10}$ M, or $10^{-11}$ M, between $10^{-8}$ M-$10^{-11}$ M, $10^{-9}$ M-$10^{-10}$ M, and $10^{-10}$ M-$10^{-11}$ M. In a preferred aspect, specific activity is measured using a competitive binding assay as set forth in Ausubel F M, (1994). Current Protocols in Molecular Biology. Chichester: John Wiley and Sons ("Ausubel"), which is incorporated herein by reference.

Obtaining a Prognosis for a Subject Having an Inflammatory or Autoimmune Disease The present invention provides assays for the detection of antibodies to PAD2 in biological samples including, e.g., but are not limited to, whole blood, plasma, serum, semen, cell lysates, saliva, tears, urine, fecal material, sweat, buccal, skin, synovial fluid, cerebrospinal fluid, and hair, from subjects with inflammatory and autoimmune conditions. This includes prognostic (or predictive) assays for determining the risk that a subject will develop a more severe form of inflammatory disease (e.g., RA). Such assays can be used for prognostic or predictive purpose, for example to select appropriate therapeutic or prophylactic compounds for a subject based on the level of AA (e.g., anti-PAD2 antibodies) in a sample obtained from the subject. The assays also can be used for disease diagnosis, including the severity of the disease, and/or monitoring the disease, including monitoring the response to a treatment. The methods described herein can also be used to determine the levels of such AAs in subjects to aid in predicting the response of such subjects to medication.

The invention provides a method for detecting antibodies to PAD2 in a subject having or suspected of having a disease comprising: a) obtaining a sample from the subject; b) providing a substrate having a first capture probe bound thereto, wherein the capture probe comprises peptidyl arginine deiminase 2 (PAD2) protein or a portion or fragment thereof which comprises an antigen recognized by autoantibodies present in the subject; c) contacting the substrate having the capture probe bound thereto with the sample from the subject; d) measuring the amount of a complex of the capture probe and the autoantibodies formed in step c); e) providing a reference level sample; and f) comparing the amount of a complex of the capture probe and the autoantibodies formed from the subject to the amount of a complex of the capture probe and the antibodies formed from the reference level sample. One application of this information is identifying the subject as having a better prognosis for not developing a more severe form of inflammation, e.g. such as a lower risk of developing a severe form of RA when the amount of a complex of the capture probe and the autoantibodies formed from the subject having RA is increased compared to the amount of a complex of the capture probe and the autoantibodies formed from the reference level sample. In some embodiments, the invention provides a method for obtaining a disease diagnosis, including, for example, diagnosis of a subject suspected of having a less severe form of RA using the methods provided herein. In some embodiments, the invention provides a method for monitoring, including therapeutic monitoring, e.g. a subject with RA, using the methods provided herein. In some embodiments, the invention provides a method for monitoring disease progression of a subject with RA, using the methods provided herein.

The capture probe includes peptidyl arginine deiminase 2 (PAD2) protein or a portion or fragment thereof. PAD2 is one of five PAD enzymes encoded by humans, and appears to drive citrullination in inflammatory and autoimmune conditions. Witalison et al., Curr Drug Targets, 16(7):700-710 (2015). PAD enzymes (e.g., PAD2) are calcium-dependent enzymes. The structure of PAD2 has been characterized. See Slade et al., ACS Chem Biol. 10(4), 1043-53 (2015). Portions or fragments of PAD2 can also be used. Portions or fragments of PAD2 include peptides comprising amino acid sequences sufficiently homologous to or derived from the amino acid sequence of a PAD2 protein, but which include less amino acids than a full length PAD2 protein. A portion or fragment of PAD2 can be a polypeptide which is, for example, 10, 25, 50, 100, 200, 300, 400, 500, or more amino acids in length. The portion or fragment of PAD2 should include at least one epitope binding by anti-PAD2 antibodies.

The evaluation of PAD2 autoantibody level can be carried out using a variety of different types of assays. In some embodiments, the method is an enzyme immunoassay method. In other embodiments, the method is a radioimmunoassay method. In further embodiments, the method is an immunoblotting method. In another embodiment, the method is a chemiluminescent immunoassay (CIA). In yet a further embodiment, the method is a particle based multi-analyte test (PMAT).

Methods and protocols for conducting immunoassays and biophysical protein-interaction assays are well known in the art. See, e.g., Wild D., The Immunoassay Handbook, Elsevier Science, 4th Edition (2013); Fu H., Protein-Protein Interactions, Humana Press, 4th Edition (2004). For example, a chemiluminescent immunoassay (CIA) is an immunoassay technique where the label, for example, the "indicator" of the analytic reaction, is a luminescent molecule. In general, luminescence is the emission of visible or near-visible ($\lambda$=300-800 nm) radiation which is generated when an electron transitions from an excited state to ground state. The resultant potential energy in the atom gets released in the form of light.

A PMAT, allows simultaneous measurement of two or more analytes in a single assay. For example, in PMAT, different types of particles are used simultaneously, with each type having immobilized a specific binding partner for a specific molecule species on the surface of its particles. In a solution, the analyte molecules to be detected are bound to their binding partners on the corresponding particle type. The bonds are then detected optically through the addition of a secondary marker that marks all particle-bound analyte molecules of the PMAT assay. A PMAT can be performed using a variety of formats known in the art, such as flow cytometry, a capture sandwich immunoassay, or a competitive immunoassay. For example, using a dual-laser flow-based detection instrument, the binding of analyte fractions, such as autoantibodies, can be detected through the fluorescence of the secondary marker. In some embodiments, the PMAT particle is a bead.

In effecting an enzymatic, fluorescence, chemical (e.g. chemiluminescence), colorimetric or PMAT immunoassay, the level of PAD2 autoantibodies is determined by providing a substrate having a first capture probe bound thereto, wherein the capture probe comprises peptidyl arginine deiminase 2 (PAD2) protein or a portion or fragment thereof which comprises an antigen recognized by autoantibodies present in the serum of subjects suffering from inflammatory conditions, such as RA. The substrate is a solid phase; examples include beads made of polystyrene, glass, etc., microplates and the like. When the PAD2 is adsorbed on the solid phase, there may preferably be employed a biological sample including PAD2 having a PAD2 concentration of 0.1 µg/ml or more. It is preferred that the PAD2 concentration be predetermined taking into consideration the sensitivity in the assay system. A preferred concentration is about 1 to 10 µg/ml.

As used herein, the term "substrate" refers to any surface capable of having capture probes bound thereto. Such surfaces include, but are not limited to, glass, metal, plastic, or materials coated with a functional group designed for binding of capture probes or analytes. Substrates also may be referred to as slides.

The capture probe can be bound to the substrate using a binding reagent, or in other embodiments, it can be non-specifically adsorbed to the substrate surface. A variety of binding reagents for adhering proteins to a substrate are known to those skilled in the art. For example, antibodies specific to the protein can be used as binding reagents. Aptamers and various chemical reagents (e.g., coupling agents, such as dialdehydes, carbodiimides, dimaleimides, bis-imidates, bis-diazotized benzidine) can also be used as binding reagents.

The PAD protein or fragment thereof thus adsorbed on the solid phase is then reacted with a biological sample (e.g., serum or plasma) of the subject. It is preferred that the sample be diluted with, for example, a sodium phosphate buffer containing a surfactant 10 to 100 times. The reaction was effected at 4° C. to 40° C., for 30 minutes to overnight, for example, at 4° C., overnight or at 37° C. for 30 minutes while preventing the evaporation of the reaction mixture. Thus, only the anti-PAD2 autoantibody in the sample is caught on the PAD2 protein adsorbed on the solid phase. The immobilized anti-PAD2 autoantibody can then be identified by labeling it with a labeled molecule that specifically binds to the anti-PAD2 autoantibody. For example, enzyme-labeled anti-human IgG antibody can be used to identify the bound anti-PAD2 autoantibody.

The enzymatic, fluorescence, chemical (e.g. chemiluminescence), colormetric, PMAT, or similar activity revealed by the labeled antibody thus bonded corresponds to the amount of autoantibody immobilized by the capture probe. Examples of suitable enzymes include alkaline phosphatase and horseradish peroxidase. Accordingly, the amount of anti-PAD2 antibody in the sample can be determined by measuring the enzyme activity. Alternately, other labels can be used instead of enzyme activity. Examples of other types of label include a radioisotope, a fluorophore (e.g., fluorescein isothiocyanate (FITC), phycoerythrin (PE)), chemiluminescence, and element particles (e.g., gold particles).

Methods for measuring the amount or presence of an antibody-PAD2 complex include, for example, detection of fluorescence, luminescence, chemiluminescence, absorbance, reflectance, transmittance, birefringence or refractive index (e.g., surface plasmon resonance, ellipsometry, a resonant mirror method, a gating coupler waveguide method or interferometry). Optical methods include microscopy (both confocal and non-confocal), imaging methods and non-imaging methods. Electrochemical methods include voltammetry and amperometry methods. Radio frequency methods include multipolar resonance spectroscopy.

As used herein, the term "sample" means sample material derived from or contacted by living cells. The term "sample" is intended to include tissues, cells and biological fluids isolated from a subject, as well as tissues, cells and fluids present within a subject. Biological samples include, e.g., but are not limited to, whole blood, plasma, serum, semen, cell lysates, saliva, tears, urine, fecal material, sweat, buccal, skin, synovial fluid, cerebrospinal fluid, and hair. Biological samples can also be obtained from biopsies of internal organs. Preferably, the biological sample is a biological fluid including autoantibodies. Biological samples can be obtained from subjects for diagnosis prognosis, monitoring, or a combination thereof, or for research, or can be obtained from un-diseased individuals, as controls or for basic research. Biological samples can be obtained by any known means including needle stick, needle biopsy, swab, and the like.

A biological sample may be fresh or stored (e.g. blood or blood fraction stored in a blood bank). Samples can be stored for varying amounts of time, such as being stored for an hour, a day, a week, a month, or more than a month. The biological sample may be a bodily fluid expressly obtained for the assays of this invention or a bodily fluid obtained for another purpose which can be sub-sampled for the assays of this invention.

As used herein, the term "reference level" is intended to mean a control level of a biomarker, e.g., disease-associated AA, used to evaluate a test level of the biomarker (e.g., PAD2 autoantibody) in a sample from an individual. A reference level can be a normal reference level in a sample from a normal subject or a disease reference level from a disease-state subject. A normal reference level is an amount of expression of a biomarker in a non-diseased subject or subjects. A disease-state reference level is an amount of expression of a biomarker in a subject with a positive diagnosis for the disease or condition. A reference level also can be a stage-specific reference level. A stage-specific reference level refers to a level of a biomarker characteristic of a given stage of progression of a disease or condition.

A subject having a decreased risk of developing a severe form of an inflammatory disease, such as RA, has a lower percentage chance of developing a severe form of an inflammatory disease in comparison with the average risk that a subject having inflammatory disease will develop a severe form of inflammatory disease. For example, a subject having a decreased risk of developing a severe form of RA can have a 5%, 10%, 15%, 20%, 25%, 30%, 40%, 45%, 50%, 60%, 70%, 80%, 90%, or 95% lower chance of developing a severe form of RA in comparison with the risk that an average subject having RA will develop a severe form of RA.

The method can also include the step of providing a report indicating the subject has a better prognosis for not developing a more severe form of inflammation, such as a lower risk of developing a severe form of RA, or is in need of therapy suitable to prevent the development of a severe RA. For example, the apparatus for carrying out the method can include a processor coupled to the protein detector and adapted to quantify the data representing the signals from the detector, and adapted to perform the multivariate statistical analysis, compare the output value to the first reference value and the second reference value, and calculate the risk score; and an output display coupled to the processor and configured to report the risk score.

The invention includes the step of providing a prognosis for a subject having RA which includes identifying the subject as having a lower risk of developing a severe form of RA when the amount of a complex of the capture probe and the autoantibodies formed from the subject having RA is increased compared to the amount of a complex of the capture probe and the autoantibodies formed from the reference level sample.

In some embodiments, the invention includes the step of diagnosing a subject suspected of having an inflammatory disease, such as RA, MS and PsA. The invention also includes diagnosing a less severe form of RA. For example, a less severe form of RA can be diagnosed when the amount of a complex of the capture probe and the autoantibodies formed from the subject having RA is increased compared to the amount of a complex of the capture probe and the autoantibodies formed from the reference level sample. In some embodiments, the invention includes the step of monitoring a subject with RA, which includes monitoring the amount of a complex of the capture probe and the autoantibodies formed from the subject having RA compared to the amount of a complex of the capture probe and the autoantibodies formed from the same subject at a previous time. In some embodiments, the monitoring can include monitoring the therapeutic response of a patient being treated for RA. In some embodiments, the monitoring can include monitoring disease progression of RA.

The lung is a common site of complications of systemic connective tissue diseases, such as RA and other connective tissue diseases. Lung involvement can present as interstitial lung disease (ILD). Connective tissue disease associated with interstitial lung disease (CT-ILD), also known as interstitial pneumonia with autoimmune features (IPAF), is a serious pulmonary complication associated with connective tissue diseases, and IPAF can indicate a more severe type of connective tissue disease. For example, severe RA involves a higher level of articular damage, and/or RA-associated conditions, such as interstitial lung disease (RA-ILD). Additional connective tissue diseases associated with the development of IPAF include, but are not limited to, systemic sclerosis (SSc), scleroderma, sarcoidosis, poly-/dermatomyositis (PM/DM), Sjögren's syndrome (SjS), systemic lupus erythematosus (SLE), and undifferentiated (UCTD) as well as mixed connective tissue disease (MCTD). The manifestation of particular connective tissue diseases, such as RA, to include features of ILD are indicators of severe forms of the disease. Thus, in some embodiments, provided herein are methods for the diagnosis, including disease severity, prognosis, and/or monitoring for various forms of IPAF such as those exemplified above and RA-ILD. Severe rheumatoid arthritis is also referred to as erosive RA, and can be identified using an X-ray evaluation of the subject which shows evidence of cartilage and/or bone destruction.

Treatment of subjects having inflammatory diseases such as RA is often more aggressive than necessary because subjects having an increased risk of developing severe RA cannot be identified. The present invention provides a method of avoiding such expensive and unnecessary treatment in subjects who have a lower risk of developing severe RA. Rheumatoid arthritis is typically treated with a disease modifying anti-rheumatic drug (DMARD) such as methotrexate. However, if the disease continues to worsen, or does not improve in 3-6 months, the treating physician may initiation combination therapy by adding additional non-biologic DMARDs or switching the patient to a second-line drug like a biological medication (e.g., a TNF-α inhibitor). However, because destruction of bone and damage to the lungs is irreversible, physicians may immediately provide more aggressive treatment such as combination therapy to help assure that severe RA does not develop.

Methods of Treat Patients with Anti-PAD2 Antibodies

Another aspect of the invention provides a method of treating a subject by administering a therapeutically effective amount of an antibody or a fragment thereof that specifically binds to peptidyl arginine deiminase 2 (PAD2) protein. Treatment of a subject having RA with anti-PAD2 protein, for example, can help avoid progression of the RA to a more severe form of RA (i.e., erosive RA). In some embodiments, the invention provides a method of treating IPAF, and/or RA-ILD in a subject by administering to the subject a therapeutically effective amount of an antibody or a fragment thereof that specifically binds to peptidyl arginine deiminase 2 (PAD2) protein.

The anti-PAD2 antibody can be any type of immunoglobulin that is known in the art. For instance, the antibody can be of any isotype, e.g., IgA, IgD, IgE, IgG, IgM, etc. The antibody can be monoclonal or polyclonal. The antibody can be a naturally-occurring antibody, e.g., an antibody isolated and/or purified from a mammal, e.g., mouse, rabbit, goat, horse, chicken, hamster, human, etc. Alternatively, the antibody can be a genetically-engineered antibody, e.g., a humanized antibody or a chimeric antibody. The antibody can be in monomeric or polymeric form.

Methods of testing antibodies for the ability to bind to antigens (e.g., PAD2 antigens) are known in the art and include any antibody-antigen binding assay, such as, for example, radioimmunoassay (RIA), ELISA, Western blot, immunoprecipitation, and competitive inhibition assays (see, e.g., Janeway et al., infra, and U.S. Patent Application Publication No. 2002/0197266 A1).

Suitable methods of making antibodies to PAD2 are known in the art. For instance, standard hybridoma methods are described in, e.g., Kohler and Milstein, Eur. J. Immunol., 5, 511-519 (1976), Harlow and Lane (eds.), Antibodies: A Laboratory Manual, CSH Press (1988), and C. A. Janeway et al. (eds), Immunobiology, 5th Ed., Garland Publishing, New York, N.Y. (2001)). Alternatively, other methods, such as EBV-hybridoma methods (Haskard and Archer, J. Immunol. Methods, 74(2), 361-67 (1984), and Roder et al., Methods Enzymol., 121, 140-67 (1986)), and bacteriophage vector expression systems (see, e.g., Huse et al., Science, 246, 1275-81 (1989)) are known in the art. Further, methods of producing antibodies in non-human animals are described in, e.g., U.S. Pat. Nos. 5,545,806, 5,569,825, and 5,714,352, and U.S. Patent Application Publication No. 2002/0197266 A1).

Phage display furthermore can be used to generate antibodies. In this regard, phage libraries encoding antigen-binding variable (V) domains of antibodies can be generated using standard molecular biology and recombinant DNA techniques (see, e.g., Sambrook et al. (eds.), Molecular Cloning, A Laboratory Manual, 3rd Edition, Cold Spring Harbor Laboratory Press, New York (2001)). Phage encoding a variable region with the desired specificity are selected for specific binding to the desired antigen, and a complete or partial antibody is reconstituted comprising the selected variable domain. Nucleic acid sequences encoding the reconstituted antibody are introduced into a suitable cell line, such as a myeloma cell used for hybridoma production, such that antibodies having the characteristics of monoclonal antibodies are secreted by the cell (see U.S. Pat. No. 6,265,150).

Antibodies can be produced by transgenic mice that are transgenic for specific heavy and light chain immunoglobulin genes. Such methods are known in the art and described in, for example U.S. Pat. Nos. 5,545,806 and 5,569,825, and Janeway et al., supra.

Humanized antibodies can be produced using synthetic and/or recombinant nucleic acids to prepare genes (e.g., cDNA) encoding the desired humanized chain. For example, nucleic acid (e.g., DNA) sequences coding for humanized variable regions can be constructed using PCR mutagenesis methods to alter DNA sequences encoding a human or humanized chain, such as a DNA template from a previously humanized variable region (see e.g., Kamman, M., et al., Nucl. Acids Res., 17: 5404 (1989)); Sato, K., et al., Cancer Research, 53: 851-856 (1993); Daugherty, B. L. et al., Nucleic Acids Res., 19(9): 2471-2476 (1991); and Lewis, A. P. and J. S. Crowe, Gene, 101: 297-302 (1991)). Using these or other suitable methods, variants can also be readily produced. In one embodiment, cloned variable regions can be mutagenized, and sequences encoding variants with the desired specificity can be selected (e.g., from a phage library; see e.g., Krebber et al., U.S. Pat. No. 5,514,548; Hoogenboom et al., WO 93/06213).

The anti-PAD2 antibody is administered in an effective amount which inhibits the activity of PAD2. For therapy, an effective amount will be sufficient to achieve the desired therapeutic (including prophylactic) effect (such as an amount sufficient to inhibit PAD2 activity). The antibody can be administered in a single dose or multiple doses. The dosage can be determined by methods known in the art and can be dependent, for example, upon the individual's age, sensitivity, tolerance and overall well-being. Suitable dosages for antibodies can be from about 0.1 mg/kg body weight to about 10.0 mg/kg body weight per treatment.

According to the method, the antibody (e.g., humanized immunoglobulin) can be administered to an individual (e.g., a human) alone or in conjunction with another agent. A humanized immunoglobulin can be administered before, along with or subsequent to administration of the additional agent. Thus, the invention includes pharmaceutical compositions comprising an anti-PAD2 antibody or fragment thereof of the invention and a suitable carrier. In one embodiment, more than one different anti-PAD2 antibody is administered. In another embodiment, an additional pharmacologically active ingredient (e.g., an agent suitable for treating rheumatoid arthritis, such as, but not limited to methotrexate, hydroxychloroquine, sulfasalazine, leflunomide, TNF-α inhibitors (certolizumab, infliximab and etanercept), abatacept, anakinra, rituximab and tocilizumab)) can be administered in conjunction with an anti-PAD2 antibody of the present invention. A variety of routes of administration are possible, including, but not necessarily limited to, parenteral (e.g., intravenous, intraarterial, intramuscular, subcutaneous injection), oral (e.g., dietary), topical, inhalation (e.g., intrabronchial, intranasal or oral inhalation, intranasal drops), or rectal, depending on the disease or condition to be treated. Parenteral administration is a preferred mode of administration.

Formulation will vary according to the route of administration selected (e.g., solution, emulsion). An appropriate composition comprising the anti-PAD2 antibody to be administered can be prepared in a physiologically acceptable vehicle or carrier. For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils. Intravenous vehicles can include various additives, preservatives, or fluid, nutrient or electrolyte replenishers (See, generally, Remington's Pharmaceutical Sciences, 17th Edition, Mack Publishing Co., PA, 1985). For inhalation, the compound can be solubilized and loaded into a suitable dispenser for administration (e.g., an atomizer, nebulizer or pressurized aerosol dispenser).

The antibody is usually administered on multiple occasions. Intervals between single dosages can be, for example, weekly, monthly, every three months or yearly. Intervals can also be irregular as indicated by measuring blood levels of antibody to the target antigen in the patient. In some methods, dosage is adjusted to achieve a plasma antibody concentration of about 1-1000 μg/ml and in some methods about 25-300 μg/ml. Alternatively, antibody can be administered as a sustained release formulation, in which case less frequent administration is required. Dosage and frequency vary depending on the half-life of the antibody in the patient. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated.

The selected dosage level will depend upon a variety of pharmacokinetic factors including the activity of the particular compositions of the present invention employed, the route of administration, the time of administration, the rate of excretion of the particular antibody being employed, the duration of the treatment, other drugs, compounds and/or materials used in combination with the particular compositions employed, the age, sex, weight, condition, general health and prior medical history of the patient being treated, and like factors well known in the medical arts.

In some embodiments, the anti-PAD2 antibody is a humanized antibody. Humanized antibodies are preferable for use in human subjects, in order to avoid generating an immune response against the antibodies themselves. Examples of humanized antibodies include those selected from the group of antibodies consisting of Fab2, Fab4, and Fab6, or variants thereof including only conservative sequence modifications.

Kits

In accordance with another embodiment, the present invention provides one or more kits for providing a prognosis, diagnosis, including the severity of the disease, and/or monitoring for a subject having an inflammatory or autoimmune disease (e.g., RA, MS and PsA), or for treating a subject having RA. In some embodiments, the present invention provides one or more kits for providing a prognosis, diagnosis, and/or monitoring for a subject having IPAF, RA-ILD, or for treating a subject having IPAF, or RA-ILD. The kits components of the kits will vary depending on whether they are intended for prognosis, diagnosis, monitoring, or treatment. Kits for prognosis, diagnosis, or monitoring comprise a substrate including a capture probe, wherein the capture probe comprises peptidyl arginine deiminase 2 (PAD2) protein, or a portion or fragment thereof. The kit also includes reagents, buffers, and the like for carrying out an immunoassay (e.g., ELISA), which are known to those of ordinary skill in the art. Kits for treatment include anti-PAD2 antibodies, or effective fragments thereof, together with a pharmaceutically acceptable carrier for administration of the antibodies. The antibody or fragment thereof that specifically binds to PAD2 can be any of the antibodies described herein. For example, in some embodiments the antibody is selected from the group of antibodies consisting of Fab2, Fab4, and Fab6, or variants thereof including only conservative sequence modifications.

Kits according to the present invention are assemblies of reagents for testing antibody binding, or administering antibodies. They are typically in a package which contains all elements, optionally including instructions. Instructions may be in any form, including paper or digital. The instructions may be on the inside or the outside of the package. The instructions may be in the form of an internet address which provides the detailed manipulative or analytic techniques. The package may be divided so that components are not mixed until desired.

Components of the kits of the present invention may be in different physical states. For example, some components may be lyophilized and some in aqueous solution. Some may be frozen. Individual components may be separately packaged within the kit. Other useful tools for performing the methods of the invention or associated testing, therapy, or calibration may also be included in the kits, including buffers, enzymes, chemiluminescence reagents, PMAT reagents, gels, plates, detectable labels, vessels, etc. Kits may-include tools for collecting suitable samples, such as tools for collecting oral swabs, oral biopsies, and endoscopes.

An example has been included to more clearly describe a particular embodiment of the invention and its associated cost and operational advantages. However, there are a wide variety of other embodiments within the scope of the present invention, which should not be limited to the particular examples provided herein.

Example

Autoantibodies to Peptidylarginine Deiminase 2 are Associated with Less Severe Disease in Rheumatoid Arthritis In this study, we found that anti-PAD2 antibodies are present in a subset of patients with RA who lack the traditional risk factors associated with severe disease, such as ACPAs and SE. Instead, they have a unique set of demographic and clinical characteristics including less progressive articular damage and lower risk of ILD. These findings have important implications in the ability to identify clinically informative patient subgroups to aid in disease prognosis and selection of appropriate therapeutic agents.

Methods

Human Subjects

Convenience sera from 100 healthy controls and 42 patients with RA from the Johns Hopkins Arthritis Center were used as a discovery sample for anti-PAD2 antibodies. Sera from 184 RA patients from the Evaluation of Subclinical Cardiovascular Disease and Predictors of Events in Rheumatoid Arthritis (ESCAPE RA) cohort were then screened for the presence of PAD2 autoantibodies by ELISA. All patients in ESCAPE RA met the American Rheumatism Association 1987 revised criteria for the classification of RA (Arnett et al., Arthritis Rheum, 31(3):315-324 (1988)) and have been extensively described previously. Giles et al., Ann Rheum Dis, 73(8):1487-1494 (2014). In brief, baseline demographic data and medication use were captured by questionnaire; anti-CCP, RF, and anti-PAD3/4 antibodies were measured as previously reported (Darrah et al., ibid); and clinical features were assessed by clinical examination. Radiographs of the hands and feet, obtained at baseline and a follow-up visit occurring 39±4 months after baseline, were scored according to the Sharp-van der Heijde method by an experienced reader blinded to clinical characteristics. The change in Sharp-van der Heijde score (SHS) between the two visits was calculated. The number of swollen joints was recorded at each study visit and the average mean swollen joint count (SJC) throughout the duration of the study was determined using an area-under-the-curve calculation. Participants underwent multidetector row computed tomography (MDCT) of the chest at the baseline visit, and the presence and extent of ILD was scored by an experienced pulmonary radiologist as previously described (Giles et al., ibid). Deidentified samples from patients with PsA and MS were also screened for anti-PAD2 antibodies. All samples were obtained under informed written consent approved by the Johns Hopkins Institutional Review Board.

PAD2 Protein Purification

Recombinant human PAD2 was expressed from the pET28a vector, generating a protein containing both N-terminal 6× Histidine and T7 tags. The protein was purified using a Ni-NTA agarose column according to manufacturer's instructions (Qiagen). Following PAD2 purification, the 6×His tag was removed by cleavage with thrombin.

Anti-PAD2 ELISA

High-binding EIA plates (Costar) were coated overnight with 200 ng/well of PAD2 in phosphate buffered saline pH 7.4 (PBS) or PBS alone. Plates were blocked with 3% non-fat milk. Patient sera were diluted 1:250 in 1% milk/PBS/0.05% tween-20 and assayed in duplicate. A known positive patient serum was serially diluted and included as a standard on each plate. Anti-PAD2 units were assigned with the highest standard representing 10 anti-PAD2 arbitrary units (AU). Anti-PAD2 antibody binding was detected using a horseradish peroxidase-conjugated anti-human IgG secondary antibody (Jackson Immunoresearch) diluted 1:7500 in PBS/0.05% Tween-20. SureBlue TMB peroxidase substrate (KPL) was added to visualize antibody binding and an equal volume of 1M hydrochloric acid was added to stop the colorimetric reaction, before determining the absorbance at 450 nm with a 560 nm reference using a Perkin Elmer Victor 3 plate reader. The 4-point standard curve formed from the serially diluted positive control sera was used to calculate anti-PAD2 AU based on the average absorbance values for each unknown serum sample using WorkOut software. The background values observed for PBS-coated wells were subtracted from the corresponding PAD2-coated wells for each sample. The threshold for positivity for each cohort was set at three standard deviations above the mean of the corresponding healthy control sera.

In Vitro Citrullination Assay

IgG was purified from the serum of 6 anti-PAD4 positive and 5 anti-PAD4 negative patients with RA using the Melon Gel IgG Spin Purification Kit (Thermo). Recombinant human PAD2 (200 nM) was pre-incubated with the purified IgG (1.5 uM) for 45 min at 4° C. in 100 mM Tris-HCl (pH 7.4). Following incubation, plasminogen-depleted fibrinogen (1 μM) (Millipore #341578) or HEK293 cell lysate in NP40 lysis buffer (250 mg/ml) was added to the PAD2/IgG mixtures and incubated at 37° C. for 90 min in the presence of 1.5 mM $CaCl_2$ and 1 mM DTT. The citrullination reaction was stopped directly by adding SDS sample buffer and boiling at 95° C. for 5 mins. Denatured proteins were separation by electrophoresis, transferred to nitrocellulose (Ponceau stain used as a loading control), and immunoblotted using respective antibodies. Mouse anti-peptidyl-citrulline antibody (Millipore, clone F95) was used to assess citrullination of substrates in the HEK293 lysate, and mouse anti-citrullinated fibrinogen (Modiquest, clone 20B2) was used to detect citrullinated fibrinogen. The blots were incubated with primary antibodies at dilution of 1:1000 overnight, followed by incubation with a goat anti-mouse secondary antibody at 1:10000 (anti-IgM isotype for F95) for 1 hour at room temperature. Antibody binding was detected using West Pico ECL reagent (Pierce) and chemiluminescence was visualized by autoradiography.

Statistical Analyses

The difference in the median anti-PAD2 AU of the RA patients compared with healthy controls was determined using a Mann-Whitney rank sum test, and the difference in anti-PAD2 positivity was determined using a 2×2 contingency table with Fisher's exact test. For analysis of demographic and clinical variables, RA patients were grouped according to the presence or absence of anti-PAD2 antibodies, and characteristics were compared using Intercooled STATA12. Student's t-tests were used for group-wise comparisons of normally distributed continuous variables; the Kruskal-Wallis test was used for group-wise comparisons of non-normally distributed variables; and Chi-squared or two-sided Fisher's exact tests, as appropriate, were used for group-wise comparisons of categorical variables. We also explored the associations of anti-PAD2 level with patient characteristics. For continuous characteristics, Spearman correlations coefficients were calculated. For dichotomous characteristics, median (IQR) anti-PAD2 levels were calculated for those with and without the dichotomous characteristics of interest, and compared using the Kruskal-Wallis test. We explored the independent association of anti-PAD2 level with radiographic progression and the frequency of radiographic ILD using multivariable ordinary logistic regression, adjusting for covariates associated with the outcomes of interest and anti-PAD2 level at the p<0.20 level in univariate modeling. A similar modeling strategy was used in the context of multivariable linear regression to explore the association of anti-PAD2 with baseline and average swollen joint counts. A two-tailed alpha=0.05 was used throughout.

Results

PAD2 is a Target of Autoantibodies in Patients with Inflammatory Diseases

To define whether IgG antibodies to PAD2 are present in patients with RA, PsA or MS, we established a PAD2 ELISA assay. Using a cutoff of three standard deviations above the mean of the healthy controls, 21.7% of RA patients in the convenience sample, 18.5% in the ESCAPE-RA cohort, 22% of PsA patients, 7% of patients with MS, and 3% of healthy controls were positive for anti-PAD2 antibodies (FIG. 1). To address the prevalence and clinical significance of anti-PAD2 antibodies in a well-defined cohort of patients with RA, sera from the longitudinal ESCAPE RA cohort (n=184) were analyzed. Anti-PAD2 antibodies were found in 18.5% of patients in the ESCAPE-RA cohort, and the median anti-PAD2 antibody level was significantly higher in the RA group compared with healthy controls (1.68 vs. 0.96 AU, respectively; p=0.0012).

Anti-PAD2 Antibodies Identify a Genetically Distinct RA Patient Subset

To determine if anti-PAD2 antibodies were associated with specific serologic, genetic, or demographic characteristics within the RA population, patients were grouped according to their anti-PAD2 antibody status and variables collected at their baseline visit were compared (summarized in Table 1). The median anti-PAD2 level by clinical characteristic is also reported in Table 2. The analysis revealed that 82% of RA patients with anti-PAD2 antibodies were female, a significantly higher proportion than present in the anti-PAD2 negative group (p=0.003) (Table 1). This corresponded to a 43% higher anti-PAD2 antibody level in female vs. male RA patients (p=0.013) (Table 2). Anti-PAD2 antibody levels were also positively associated with age (r=0.183) (Table 2). Importantly, individuals with anti-PAD2 antibodies were significantly less likely to have SE alleles compared with anti-PAD2 negative patients (53% vs. 74%, respectively) (Table 1), corresponding to a 36% lower anti-PAD2 level in patients with SE alleles (p=0.02). Anti-PAD2 antibodies were not associated with other known serologies including anti-CCP, RF, or anti-PAD3/4 antibodies (Table 1).

Anti-PAD2 Antibodies Identify Patients with Less Severe Baseline Joint Inflammation and Lung Involvement.

Figures 2A, 2B, 2C, 2D:
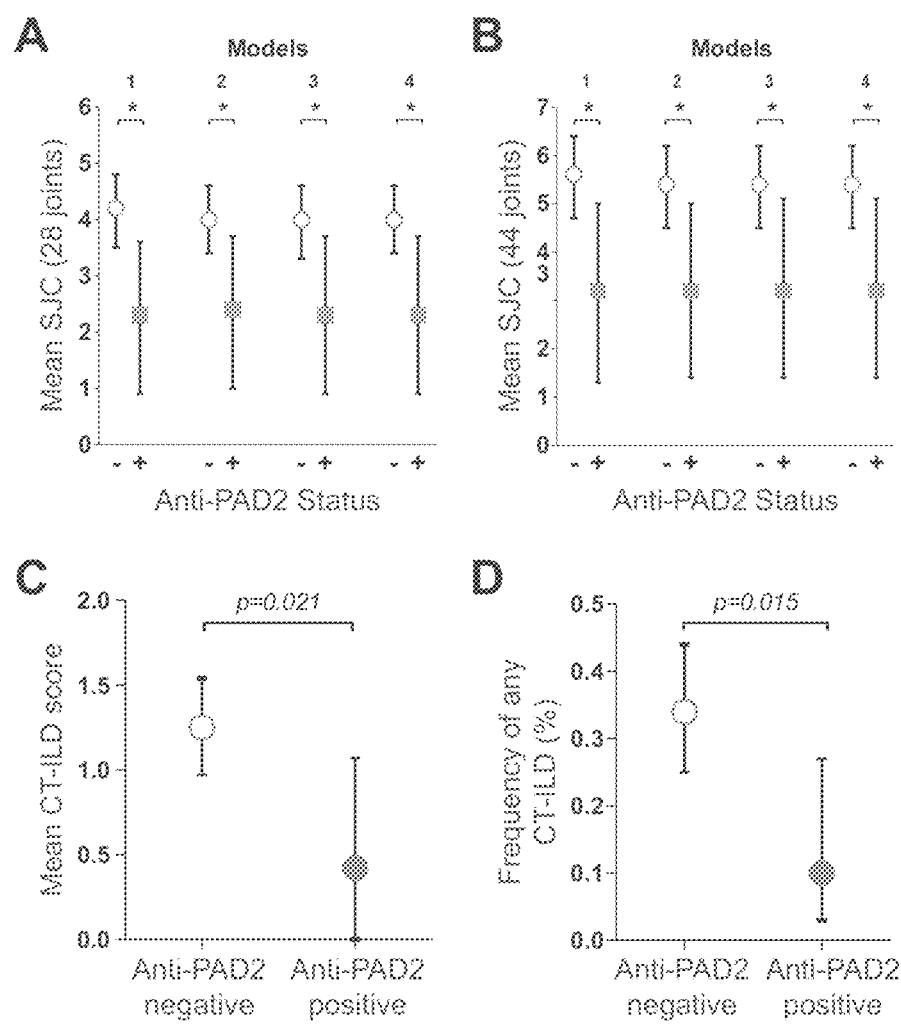
FIGS. 2A-2D provide graphs showing anti-PAD2 antibodies are associated with fewer swollen joints and less ILD. Baseline mean SJC of 28 (A) or 44 (B) joints, mean CT-ILD score (C), and adjusted frequency of ILD (D) according to anti-PAD2 antibody status is shown. (A and B) Model 1 is unadjusted. Model 2 is adjusted for sex, BMI, RA duration, HAQ, biologic use. Model 3 is additionally adjusted for RF, anti-CCP, anti-PAD3/4, and SE. Model 4 is additionally adjusted for CRP. (D) Adjusted for age, ever and current smoking, RF, anti-CCP, anti-PAD3/4, DAS28, and current biologic use. (A-D) The average values group 95% confidence intervals, and error bars are shown. A p-value <0.05 was considered significant (*).

Analysis of baseline clinical variables revealed that patients with anti-PAD2 antibodies had a significantly lower median swollen joint count (SJC) at baseline, compared to those without anti-PAD2 (2 vs. 4 joints, respectively; p=0.049) (Table 1). This was observed whether 28 or 44 joints were evaluated (FIGS. 2A and B). The presence of radiographic ILD was also less prevalent in anti-PAD2 antibody positive versus negative patients (18% vs. 36%, respectively; p=0.06) (Table 1), and antibody levels were 21% lower in patients who had ILD (p=0.039) (Table 2). It is important to note that the average ILD score among patients in the ESCAPE RA was low, since patients were classified as having radiographic ILD if any features of ILD were seen on MDCT, irrespective of clinical symptoms. Giles et al., PLoS One, 9(6):e98794 (2014). The lower frequency of ILD associated with anti-PAD2 was primarily driven by a difference in the finding of a dominant pattern of ground glass opacification (GGO) on CT. While 20 of the 131 anti-PAD2 negative patients (15%) had GGO as the predominant ILD pattern, 0% of the anti-PAD2 positive individuals (p=0.026) had this radiographic finding. In contrast, 31 of the 131 patients (24%) without anti-PAD2 antibodies had reticulation, honeycombing, or traction bronchiectasis as their predominant ILD pattern, compared with 5 of the 27 (19%) patients with anti-PAD2 antibodies (p=0.80). As such, the CT-ILD score was 66% lower in patients with anti-PAD2 antibodies compared to those who were anti-PAD2 negative (p=0.021, FIG. 2C).

It is notable that anti-PAD2 antibody levels were 25% higher in people who were receiving treatment with biologic disease modifying antirheumatic drugs (DMARDs) at the time of the study (Table 2, p=0.039), but the percentage of patients on biological DMARDs did not differ between the anti-PAD2 positive and negative groups (Table 1, p=0.17). In addition, anti-PAD2 antibody levels did not significantly differ based on treatment with non-biologic medications or glucocorticoids (Table 2).

Multivariable models were developed to define the independent contribution of anti-PAD2 antibodies to baseline joint counts and CT-ILD features. After adjusting for sex, body-mass index (BMI), disease duration, health assessment questionnaire (HAQ), biological DMARD use, known serologies, presence of SE alleles, and C-reactive protein (CRP) levels in reduced and fully adjusted models, anti-PAD2 antibodies were independently associated with fewer swollen joints on baseline 28- and 44-count joint exams (FIGS. 2A and B). Similarly, after adjusting for age, smoking history, known RA serologies, DAS28, and current biologic use, anti-PAD2 antibodies remained strongly and significantly associated with a lower frequency of ILD ($_{adj}$OR=0.24; p=0.017) (FIG. 2D). These data suggest that the effect of anti-PAD2 on joint inflammation and ILD is not due to treatment with biologic DMARDs or other confounding clinical variables.

TABLE 1

Characteristics of RA patients according to anti-PAD2 antibody status

| | Anti-PAD2 Negative n = 150 | Anti-PAD2 Positive n = 34 | p-value |
|---|---|---|---|
| Demographic features | | | |
| Age, years, mean ± SD | 61 ± 8 | 63 ± 9 | 0.28 |
| Male gender, n (%) | 68 (45) | 6 (18) | 0.003 |
| Caucasian, n (%) | 131 (87) | 28 (82) | 0.44 |
| Ever smoking, n (%) | 88 (59) | 21 (62) | 0.74 |
| Current smoking, n (%) | 18 (12) | 2 (6) | 0.38 |
| Serologic and genetic features | | | |
| RF positivity > 40 units, n (%) | 96 (64) | 22 (65) | 0.94 |
| Anti-CCP positivity > 20 units, n (%) | 113 (76) | 26 (76) | 0.94 |
| Anti-PAD3/4 XR positivity, n (%) | 17 (11) | 3 (9) | 0.66 |
| Any HLA-DRB1 SE alleles, n (%) | 110 (74) | 18 (53) | 0.014 |
| Clinical features | | | |
| RA duration, years, median (IQR) | 8 (4-17) | 9.5 (7-19) | 0.089 |
| DAS28, median (IQR) | 3.3 (2.5-4.0) | 3.2 (2.5-3.9) | 0.47 |
| HAQ score (0-3), median (IQR) | 0.75 (0.12-1.44) | 1.0 (0.12-1.50) | 0.19 |
| CRP, mg/L, median (IQR) | 2.9 (1.0-7.2) | 3.3 (1.0-7.3) | 0.91 |
| Swollen joint count, median (IQR) | 4 (2-8) | 2 (1-6) | 0.049 |
| Tender joint count, median (IQR) | 5 (2-14) | 5 (2-12) | 0.88 |
| Nodules, n (%) | 30 (21) | 3 (9) | 0.13 |
| Any ILD, n (%) | 50 (36) | 5 (18) | 0.060 |
| Total SvdH Score, median (IQR) | 7 (1-42) | 12 (0-55) | 0.91 |
| Total erosion score, median (IQR) | 3 (0-14) | 3 (0-21) | 0.83 |
| Total JSN score, median (IQR) | 5 (0-27) | 8 (0-28) | 0.69 |
| Δ SvdH Score (per year), median (IQR)* | 0.34 (0-2.1) | 0 (0-1.18) | 0.15 |
| Any increase in SvdH score, n (%)* | 69 (58) | 13 (43) | 0.15 |
| Current treatment | | | |
| Non-biologic DMARDs, n (%) | 123 (83) | 31 (91) | 0.30 |
| Biologic DMARDs, n (%) | 64 (43) | 19 (56) | 0.17 |
| Glucocorticoids, n (%) | 60 (40) | 13 (38) | 0.85 |
| Cumulative prednisone, g, median (IQR) | 3.2 (0.5-8.7) | 3.0 (0-11.7) | 0.63 |

SD = standard deviation;
IQR = interquartile range;
RF = rheumatoid factor;
DAS = disease activity score;
HAQ = health assessment questionnaire;
CRP = C-reactive protein;
SvdH = Sharp van der Heijde
*Follow-up radiographs were available in n = 149

TABLE 2

Associations of anti-PAD2 antibody levels with patient characteristics

| | Median (IQR) anti-PAD2 Level in Patient | | Spearman's | |
|---|---|---|---|---|
| | Without Characteristic | With Characteristic | Rho | p-value |
| Demographic features | | | | |
| Age, years | | | 0.183 | 0.013 |
| Male gender | 1.94 (0.99-4.54) | 1.36 (0.80-2.78) | | 0.013 |
| Caucasian | 2.39 (1.53-3.65) | 1.58 (0.84-3.35) | | 0.097 |
| Ever smoking | 1.97 (0.99-3.26) | 1.47 (0.85-3.39) | | 0.36 |
| Current smoking | 1.85 (0.95-3.41) | 0.90 (0.62-3.05) | | 0.069 |
| Serologic and genetic features | | | | |
| RF positivity | 1.57 (0.74-3.40) | 1.80 (0.95-3.35) | | 0.30 |
| Anti-CCP positivity | 1.39 (0.79-3.20) | 1.86 (0.92-3.40) | | 0.44 |
| Anti-PAD3/4 XR positivity | 1.64 (0.87-3.42) | 1.65 (0.93-2.38) | | 0.59 |
| Any HLA-DRB1 SE alleles | 2.41 (1.06-5.46) | 1.54 (0.86-3.11) | | 0.020 |
| Clinical features | | | | |
| RA duration, years | | | 0.135 | 0.068 |
| DAS28 | | | −0.003 | 0.96 |
| HAQ score (0-3) | | | 0.097 | 0.19 |
| CRP, mg/L | | | 0.029 | 0.70 |
| Swollen joint count | | | −0.106 | 0.16 |

TABLE 2-continued

Associations of anti-PAD2 antibody levels with patient characteristics

| | Median (IQR) anti-PAD2 Level in Patient | | Spearman's | |
| --- | --- | --- | --- | --- |
| | Without Characteristic | With Characteristic | Rho | p-value |
| Tender joint count | | | −0.026 | 0.73 |
| Nodules | 1.75 (0.93-3.40) | 1.86 (0.69-2.67) | | 0.039 |
| Any ILD | 1.85 (0.98-3.42) | 1.46 (0.71-2.73) | | 0.76 |
| Total SvdH Score | | | 0.022 | 0.87 |
| Total erosion score | | | −0.012 | 0.46 |
| Total JSN score | | | 0.055 | 0.75 |
| Δ SvdH Score (per year) | | | −0.027 | 0.87 |
| Any increase in SvdH score | 1.88 (0.71-4.78) | 1.78 (0.95-3.21) | | |
| Current treatment | | | | |
| Non-biologic DMARDs | 1.58 (1.06-2.59) | 1.71 (0.87-3.35) | | 0.97 |
| Biologic DMARDs | 1.54 (0.77-3.06) | 1.92 (1.20-3.96) | | 0.036 |
| Glucocorticoids | 1.68 (0.92-3.65) | 1.64 (0.84-3.21) | | 0.40 |
| Cumulative prednisone, g | | | −0.020 | 0.79 |

Figures 3A, 3B, 3C:
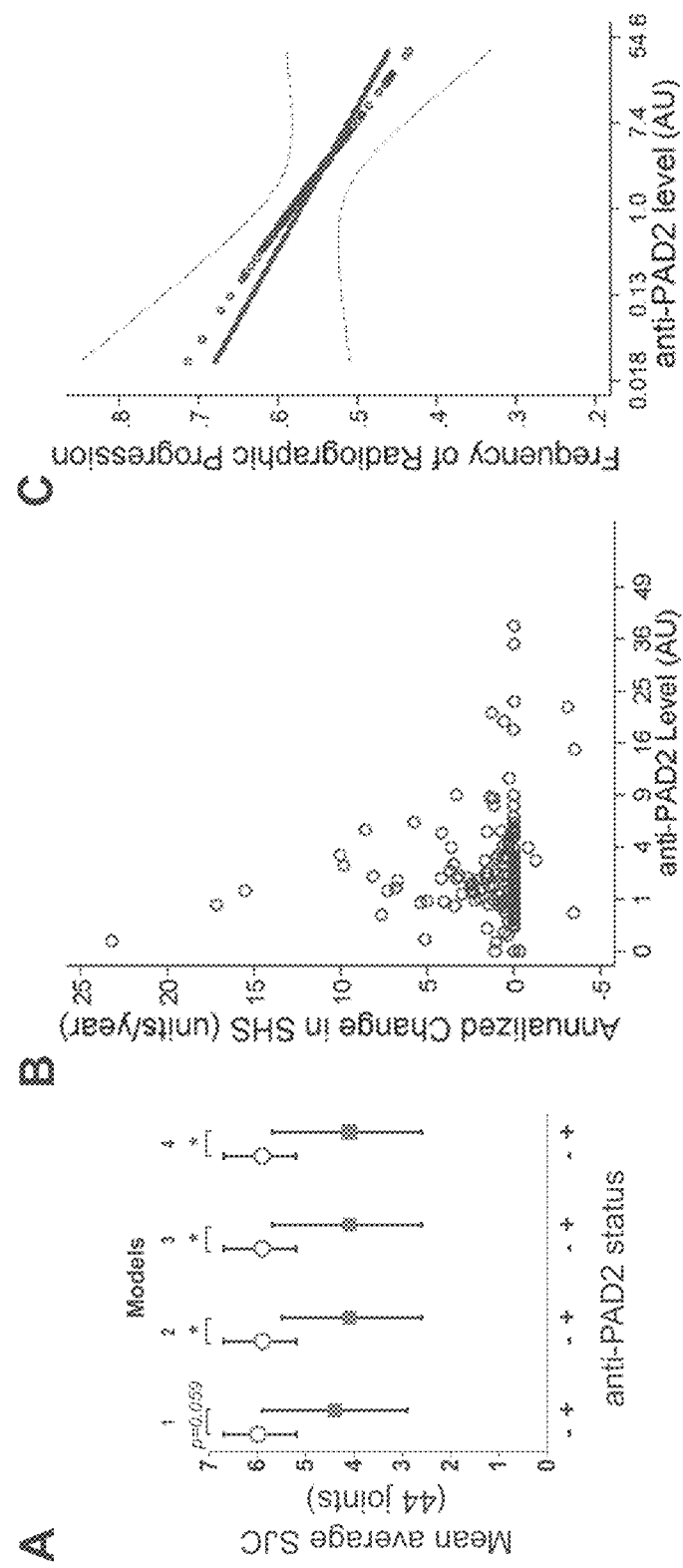
FIGS. 3A-3C provide graphs showing anti-PAD2 antibodies are inversely associated with progressive joint damage. (A) Mean average SJC for RA patients at all three visits is shown according to their anti-PAD2 antibody status. The models are adjusted for the covariates indicated in FIGS. 2A and B. (B) Yearly change in SHS is plotted versus anti-PAD2 units for each patient. (C) Anti-PAD2 antibody level was plotted against the frequency of radiographic progression in unadjusted (circles) and adjusted (line) models, and the least squares estimate of the association from multivariable linear regression with its associated 95% confidence interval (gray dotted line) is shown. A p-value <0.05 was considered significant (*). AU=arbitrary units FIGS. 4A and 4B provide images showing Anti-PAD2 antibodies do not alter PAD2 activity in vitro. PAD2 was pre-incubated with IgG from anti-PAD2 positive (lanes 3-8) or negative (lanes 9-13) patients, or no IgG (lane 1) prior to incubation with (A) purified human fibrinogen or (B) HEK293 cell lysate in the presence of 1.5 mM $CaCl_2$ and 1 mM DTT. Immunoblotting was performed using (A) mouse anti-citrullinated fibrinogen antibody clone 20B2 or (B) mouse anti-peptidyl-citrulline antibody clone F95. Human IgG light chain (IgG-Lc), and a portion of the Ponceau-stained membrane (prior to immunoblotting) is shown as a loading control. (A) The alpha, beta, and gamma isoforms of fibrinogen are indicated. Data is representative of two independent experiments.

IQR = interquartile range;
RF = rheumatoid factor;
DAS = disease activity score;
HAQ = health assessment questionnaire;
CRP = C-reactive protein;
SvdH = Sharp van der Heijde Anti-PAD2 Antibodies are Inversely Associated with the Progression of Joint Disease Since anti-PAD2 antibodies were independently associated with fewer swollen joints at baseline, they may also be independent markers of a less severe or less progressive arthritis phenotype. This hypothesis is supported by the finding that the average SJC, measured at three distinct time points throughout the duration of the study, was significantly lower in patients with anti-PAD2 antibodies, even in reduced and adjusted multivariable models (FIG. 3A). Furthermore, the yearly change in SHS, a radiographic measure of joint damage, was negatively associated with anti-PAD2 antibody level where, on average, each anti-PAD2 unit was associated with 0.08 SHS unit per year lower rate of radiographic progression (i.e. β=−0.08; p=0.028) (FIG. 3B). In a multivariable model adjusting for average CRP level, baseline SHS, and baseline adiponectin level, each log unit higher level of anti-PAD2 was associated with a 9% lower odds of radiographic joint disease progression (adjOR=0.91; p=0.016) (FIG. 3C). Importantly, biologic DMARDs were not associated with protection from progression of radiographic joint damage in the univariate models, suggesting that the association of anti-PAD2 antibodies with less progressive joint disease is independent of treatment with biological DMARDs.

The Effect of Anti-PAD2 Antibodies on PAD2 Enzymatic Activity In Vitro

Figures 4A, 4B:
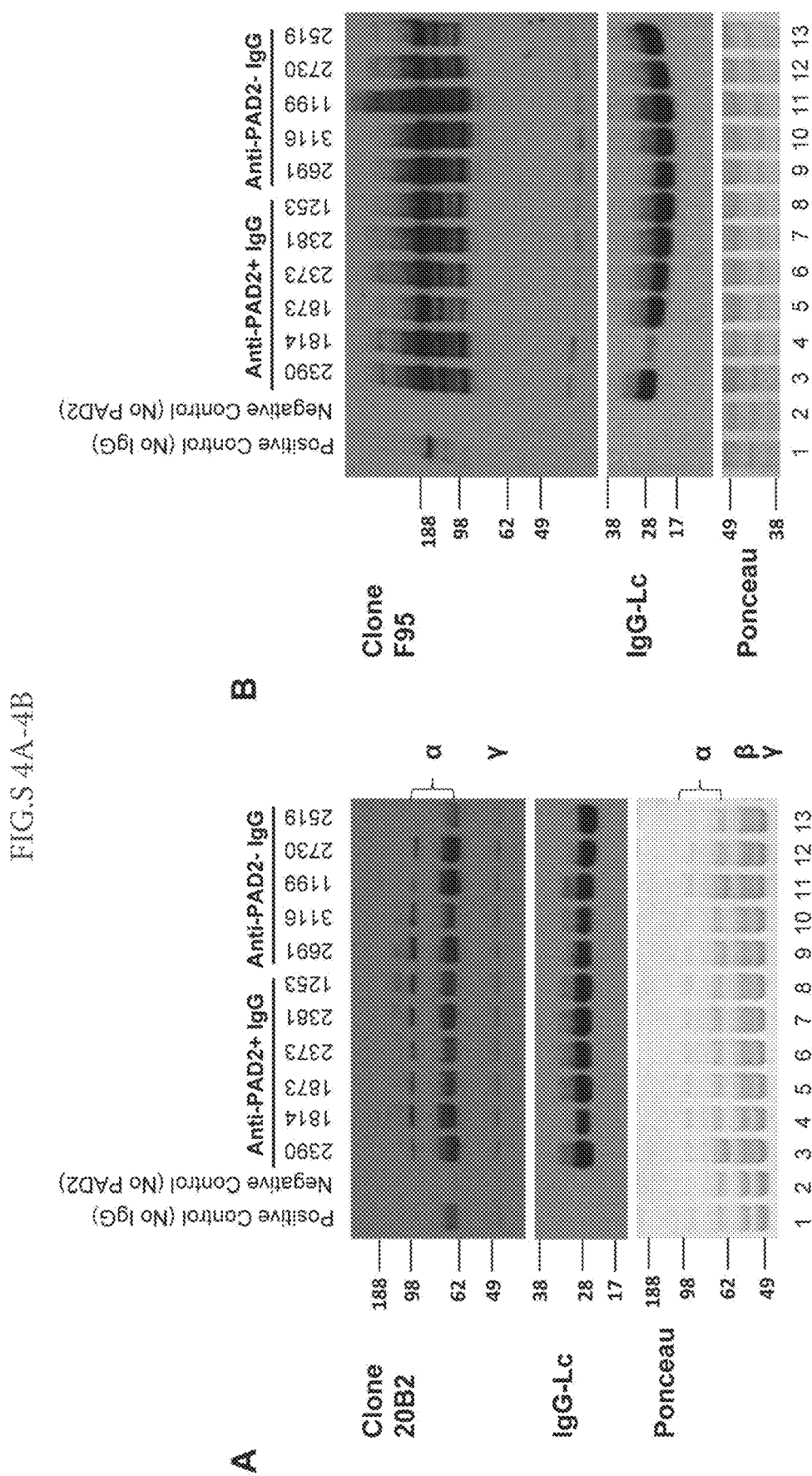

To define the potential mechanism whereby anti-PAD2 antibodies may contribute to a milder RA phenotype, two assays were established to directly address whether the antibodies inhibit PAD2 enzymatic activity. First, the effect of anti-PAD2 antibodies on PAD2-mediated citrullination of fibrinogen, a well-established extracellular substrate of PAD2 (Damgaard et al., Arthritis Res Ther, 16(6):498 (2014)), was determined. Second, the ability of anti-PAD2 antibodies to modulate PAD2-mediated citrullination of cellular substrates in HEK293 cell lysates was explored, as this may mimic PAD2-induced extracellular citrullination of proteins released from dying cells. Interestingly, IgG purified from patients with anti-PAD2 antibodies did not alter PAD2 enzyme activity relative to IgG from anti-PAD2 negative individuals when assessed for citrullination of purified fibrinogen (FIG. 4A) or HEK293 cell lysate (FIG. 4B).

Discussion

Prognostic biomarkers for assigning risk of specific clinical outcomes in patients with RA are not currently available for use in clinical practice. Anti-PAD2 antibodies may represent such a clinical biomarker as they are not associated with traditional genetic or serologic RA risk factors, including SE alleles, ACPAs, and RF. Instead, patients with antibodies to PAD2 had fewer swollen joints on exam, less evidence of radiographic ILD, and experienced less progression of radiographic joint damage. The ability to identify patients who may have less severe lung and joint disease is an important step toward the management of patients with RA, including minimizing risk of exposure to therapeutics with potentially dangerous side effects and lowering overall health care costs.

From a mechanistic perspective, the negative association of anti-PAD2 antibodies with SE and lack of association with previously reported serologies, suggests a unique mechanism for the development of these antibodies. Future studies are needed to determine if there are specific genetic, stochastic, or environmental factors that lead to the developed of anti-PAD2 antibodies in patients with RA. Importantly, PAD2 is highly expressed in neutrophils (9), the most abundant inflammatory cell type in the RA joint. Malinin et al., Am J Clin Pathol, 47(2):203-208 (1967). Factors that contribute to neutrophil damage or hyperactivation may promote an abnormal release of PAD2 into the extracellular environment, which could lead to the development of anti-PAD2 antibodies. In this regard, PAD2 is found extracellularly in RA synovial fluid likely released from damaged or dying cells (Kinloch et al., Arthritis Rheum 58(8):2287-2295 (2008)), and a recent report demonstrated that PAD2 is spontaneously secreted by neutrophils into the extracellular space. Zhou et al., Front Immunol, 8:1200 (2017). These mechanisms may therefore contribute to increasing PAD2 antigen load in the RA synovial microenvironment and promote the generation of anti-PAD2 autoantibodies.

The findings that anti-PAD2 antibodies are associated with less inflammatory and progressive joint disease and a lower frequency of CT-ILD sets them apart from other RA autoantibodies described to date. Interestingly, unlike the previously described agonistic PAD3/4 cross reactive antibodies, we found that anti-PAD2 IgG had no effect on the catalytic activity of PAD2. While we cannot exclude the possibility that these findings result from limitations in our in vitro assays, it is possible that anti-PAD2 antibodies exert protective effects in RA via mechanisms besides direct inactivation of the enzyme. For example, these antibodies may promote more efficient clearance of extracellular PAD2 by phagocytes, which may decrease the enzyme concentration in the rheumatoid joint, thereby reducing pathogenic PAD2-mediated citrullination.

The observational nature of the ESCAPE RA cohort and long average disease duration preclude us from answering questions related to treatment response outcomes and the prognostic potential of anti-PAD2 antibodies in early RA. Further studies with longitudinal assessment of PAD2 autoantibody levels and clinical trials assessing the role of anti-PAD2 antibodies in predicting treatment response to specific DMARDs are warranted. The discovery of anti-PAD2 antibodies that are not associated with traditional RA risk factors but are associated with fewer swollen joints, less radiographic ILD, and less progressive joint damage has important prognostic and mechanistic implications in RA.

The complete disclosure of all patents, patent applications, and publications, and electronically available material cited herein are incorporated by reference. The foregoing detailed description and examples have been given for clarity of understanding only. No unnecessary limitations are to be understood there from. The invention is not limited to the exact details shown and described, for variations obvious to one skilled in the art will be included within the invention defined by the claims.

What is claimed is:

1. A method for detecting anti-PAD2 antibodies in a subject having Rheumatoid arthritis (RA), comprising:
    a) obtaining a biological sample from a subject, wherein the biological sample is blood, plasma, serum, or saliva;
    b) providing a substrate having a first capture probe bound thereto, wherein the capture probe comprises peptidyl arginine deiminase 2 (PAD2) protein or a portion or fragment thereof which comprises an antigen recognized by autoantibodies present in subjects;
    c) contacting the substrate having the capture probe bound thereto with the biological sample from the subject;
    d) measuring the amount of a complex of the capture probe and the anti-PAD2 antibodies formed by step c);
    e) providing a reference level sample;
    f) comparing the amount of a complex of the capture probe and the anti-PAD2 antibodies formed from the subject to the amount of a complex of the capture probe and antibodies formed from the reference level sample; and
    g) identifying the subject as having a better prognosis for not developing a more severe form of RA when the amount of a complex of the capture probe and the anti-PAD2 antibodies formed from the subject is increased compared to the amount of a complex of the capture probe and the antibodies formed from the reference level sample; and
    h) providing a less aggressive form of treatment of inflammation to the subject identified as having a better prognosis for not developing a more severe form of RA.

2. The method of claim 1, wherein the method is an enzyme immunoassay method.

3. The method of claim 1, wherein the method is a radioimmunoassay method.

4. The method of claim 1, wherein the method is an immunoblotting method.

5. The method of claim 1, wherein the capture probe is bound to the substrate with a binding reagent.

6. The method of claim 1, wherein the biological sample is serum.

7. The method of claim 1, wherein the subject is human.

* * * * *